US009492558B2

(12) United States Patent
Costantino

(10) Patent No.: US 9,492,558 B2
(45) Date of Patent: Nov. 15, 2016

(54) COMBINED MENINGOCOCCAL CONJUGATES WITH COMMON CARRIER PROTEIN

(75) Inventor: Paolo Costantino, Siena (IT)

(73) Assignee: GlaxoSmithKline Biologicals SA, Rixensart (BE)

(*) Notice: Subject to any disclaimer, the term of this patent is extended or adjusted under 35 U.S.C. 154(b) by 2289 days.

(21) Appl. No.: 11/587,101

(22) PCT Filed: Apr. 29, 2005

(86) PCT No.: PCT/IB2005/001536
§ 371 (c)(1),
(2), (4) Date: Oct. 24, 2007

(87) PCT Pub. No.: WO2005/105141
PCT Pub. Date: Nov. 10, 2005

(65) Prior Publication Data
US 2008/0254057 A1 Oct. 16, 2008

(30) Foreign Application Priority Data

Apr. 30, 2004 (GB) .................................. 0409745.7

(51) Int. Cl.
A61K 47/48 (2006.01)
A61K 39/095 (2006.01)
A61K 39/00 (2006.01)
A61K 39/116 (2006.01)

(52) U.S. Cl.
CPC ......... *A61K 47/4833* (2013.01); *A61K 39/095* (2013.01); *A61K 39/116* (2013.01); *A61K 47/48261* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| 6,248,334 B1 * | 6/2001 | Lees et al. ................ 424/236.1 |
| 6,284,250 B1 * | 9/2001 | Lees et al. ................ 424/193.1 |
| 7,118,757 B1 * | 10/2006 | Seid et al. ................ 424/250.1 |
| 2003/0068336 A1 * | 4/2003 | Ryall ........................ 424/250.1 |

FOREIGN PATENT DOCUMENTS

| EP | 1587537 | 10/2005 |
| GB | 0323103.2 | 10/2003 |
| GB | 0526412.2 | 12/2005 |
| WO | WO 96/40242 | 12/1996 |
| WO | WO-98/51339 A1 | 11/1998 |
| WO | WO 00/25812 | 5/2000 |
| WO | WO-00/56360 A2 | 9/2000 |
| WO | WO-0141800 | 6/2001 |
| WO | WO-02/00249 A2 | 1/2002 |
| WO | WO-02058737 | 8/2002 |
| WO | WO-02080965 | 10/2002 |
| WO | WO-03007985 | 1/2003 |
| WO | WO-2004067030 | 8/2004 |
| WO | WO-2005/033148 A1 | 4/2005 |

OTHER PUBLICATIONS

Paoletti PC. Vaccine 19: 2118-2126, 2001.*
Ferreccio et al. Pediatr. Infect. Dis. J. 10: 764-771, 1991.*
Menomune Product Information, Aventis Pasteur Inc., Swiftwater, PA, USA, AHFS Category 80:12, pp. 1-5, Feb. 2001.*
Rennels et al. Ped. Infect. Dis. J. 21: 978-979, Oct. 2002.*
Lamb, D. et al, "Capillary electrophoretic analysis of meningococcal polysaccharide . . . " Physico-Chemical Procedures for the Characterization of Vaccines, 103: 251-258 (2000).
Anderson et al. (1994). "Safety and Immunogenicity of Meningococcal A and C Polysaccharide Conjugate Vaccine in Adults," Infection and Immunity 62(8):3391-3395.
Beuvery et al. (1983). "Immunological Evaluation of Meningococcal Group C Polysaccharide-Tetanus Toxoid Conjugate in Mice," Infection and Immunity 41(2):609-617.
Burrage et al. (2002). "Effect of Vaccination with Carrier Protein on Response to Meningococcal C Conjugate Vaccines and Value of Different Immunoassays as Predictors of Protection," Infection and Immunity 70(9):4946-4954.
Campbell (2002). "Safety, Reactogenicity, and Immunogenicity of a Tetravalent Meningococcal Polysaccharide-Diphtheria Toxoid Conjugate Vaccine Given to Healthy Adults," The Journal of Infectious Diseases 186:1848-51.
European Pharmacopoeia Quarterly Forum Publication (2000), 3rd edition. 10 pages.
Hsieh (2000). "Characterization of Saccharide-CRM197 Conjugate Vaccines," Brown et al. (eds): Physico-Chemical Procedures for the Characterization of Vaccines. Dev Biol. Basel, Karger. 2000, vol. 103. pp. 93-104.
Lee et al. (2007). "Long-Term Thermal Stability of Group C Meningococcal Polysaccharide-Tetanus Toxoid Conjugate Vaccine," Human Vaccines 3:1, 27-32.
Menactra (Aug. 2006). "Meningococcal (Groups A, C, Y and W-135) Polysaccharide Diphtheria Toxoid Conjugate Vaccine," Sanofi Pasteur Limited, 35 pages.
North American Vaccine Files for UK Regulatory Approval of NeisVac-Ctm. Jan. 24, 2000. PR Newswire. 4 pages.

(Continued)

Primary Examiner — S. Devi
(74) Attorney, Agent, or Firm — Morrison & Foerster LLP

(57) ABSTRACT

Carrier-induced epitopic suppression is of particular concern where multiple conjugates with the same carrier protein are administered simultaneously. To avoid the suppression, the invention minimizes the amount of unconjugated carrier protein in a vaccine. The invention provides a composition for immunizing a patient against a disease caused by *Neisseria meningitidis*, wherein (1) the composition comprises conjugates for at least two of the four meningococcal serogroups A, C, W135 and Y, where at least two of the conjugates have a common carrier protein; and (2) the composition includes the common carrier in an unconjugated form at less than 10 μg/ml.

37 Claims, No Drawings

(56) References Cited

OTHER PUBLICATIONS

Notice of opposition against the grant of European Patent No. EP 1755662, granted on Aug. 12, 2009. 26 pages.
Castillo de Febres et al., (1994). "Enhanced antibody response in Venezuelan infants immunized with *Haemophilus influenzae* type b-tetanus toxoid conjugate vaccine" The Pediatric Infectious Disease Journal 13(7):635-639.
Dagan et al. (1998). "Reduced response to multiple vaccines sharing common protein epitopes that are adminstered simultaneously to infants," Infect Immun, 66(5):2093-8.
Decision of Board of Appeal, filed in relation to EP1755662, dated Jun. 25, 2015, 18 pages.
Decision revoking EP1755662, filed in opposition against EP1755662, dated Feb. 19, 2013, 24 pages.
Decker (2004) "Combination Vaccines (chapter 29)" from Vaccines, 4th Edition, Sanders, Philadelphia, US, pp. 825-861.
Declaration of Dr. Ralph Biemans, filed in opposition against EP1755662, dated Apr. 23, 2012, 3 pages.
European Pharmacopoeia, Third Edition (Jun. 1996), Pharmeuropa, pp. 1155-1157.
Granoff (2004) "Meningococcal Vaccines (chapter 34)" from Vaccines, 4th Edition, Sanders, Philadelphia, US, pp. 959-987.
Interlocutory Decision of Boards of Appeal, filed in opposition against EP1755662, dated Mar. 28, 2014, 13 pages.
Kao, (2004). "Quantification of O-acetyl, N-acetyl and phosphate groups and determination of the extent of 0-acetylation in bacterial vaccine polysacchairdes by high-performance anion exchange chromatography with conductivity detection (HPAEC-CD)" Vaccine 22(3-4):335-344.
Insel, (1995). "Potential alterations in immunogenicity by combining or simultaneously administering vaccine components" Annals New York Academy of Sciences 754:35-47.
Menjugate TM vaccine, summary of Product Characteristics, filed in opposition against EP1755662, 8 pages.
Notice of Appeal, filed in opposition against EP1755662, dated May 1, 2013, 1 page.
PR Newswire "North American Vaccine Files for UK Regulatory Approval of NeisVac-C™", Jan. 24, 2000.
Reddin et al. (2001). "Bordetella pertussis fimbriae are effective carrier proteins in Neisseria meningitidis serogroup C conjugate vaccines," FEMS Immunol Med Microbial. 31(2):153-62.
Response to Appeal by GlaxoSmithKline Biologicals SA, filed in opposition against EP1755662, dated Nov. 15, 2013, 53 pages.
Response to opposition by Novartis Vaccines and Diagnostics S.R.I., filed in opposition against EP1755662, dated Dec. 31, 2010, 12 pages.
Schneerson, (1984). "Serum antibody responses of juvenile and infant rhesus monkeys injected with *Haemophilus influenzae* type b and pneumococcus type 6A capsular polysaccharide-protein conjugates" Infection and Immunity 45(3):582-591.
Schutze et al. (1985). "Carrier-induced epitopic suppression, a major issue for future synthetic vaccines," J Immunol, 135(4):2319-22.
Statement of Grounds of Appeal, filed in opposition against EP1755662, dated Jul. 1, 2013, 22 pages.
Table of calculations relating to WO 03/07985, filed in opposition against EP1755662, 1 page.
WHO Technical Report Series, 52nd Report, (2004) WHO expert committee on biological standardization, 242 pages.
Written submissions by GlaxoSmithKline Biologicals, filed in opposition against EP1755662, dated Apr. 23, 2012, 31 pages.

* cited by examiner

COMBINED MENINGOCOCCAL CONJUGATES WITH COMMON CARRIER PROTEIN

RELATED APPLICATIONS

This application is the U.S. National Phase of International Application No. PCT/IB2005/001536, filed Apr. 29, 2005 and published in English, which claims priority to Great Britain Application No. 0409745.7, filed Apr. 30, 2004. The teachings of the above applications are incorporated herein in their entirety by reference.

All documents cited herein are incorporated by reference in their entirety.

TECHNICAL FIELD

This invention concerns vaccines against *Neisseria meningtitidis*. In particular, it concerns vaccines based on conjugated capsular saccharides from multiple meningococcal serogroups.

BACKGROUND ART

Based on the organism's capsular polysaccharide, twelve serogroups of *N. meningitidis* have been identified (A, B, C, H, I, K, L, 29E, W135, X, Y and Z). Group A is the pathogen most often implicated in epidemic disease in sub-Saharan Africa. Serogroups B and C are responsible for the vast majority of cases in USA and in most developed countries. Serogroups W135 and Y are responsible for the remaining cases in USA and developed countries.

A bivalent vaccine of capsular polysaccharides from serogroups A+C is available as the product Mencevax AC™, and tetravalent mixtures of the saccharides from serogroups A+C+Y+W135 are available as the products Mencevax ACWY™ and Menomune™ [1-3]. Although effective in adolescents and adults, these vaccines induces a poor immune response and short duration of protection, because unconjugated polysaccharides are T cell-independent antigens that induce a weak immune response which cannot be boosted.

To address the poor immunity of capsular saccharides, conjugate vaccines have been developed, where the saccharides are linked to carrier proteins. Conjugate vaccines against serogroup C have been approved for human use, and include Menjugate™ [4], Meningitec™ and NeisVac-C™. Mixtures of conjugates from serogroups A+C have also been tested [5,6], and mixtures of conjugates from serogroups A+C+W135+Y have been reported [7-10].

Although the mixed conjugate vaccines are similar to the mixed saccharide vaccines, there are some key differences. In particular, the inclusion of a carrier protein in the conjugate mixtures presents new risks, particularly in terms of carrier-induced epitopic suppression (or "carrier suppression", as it is generally known) i.e. the phenomenon whereby immunisation of an animal with a carrier protein prevents that animal from later eliciting an immune response against an antigenic epitope that is presented on that carrier [11]. This issue is of particular concern where multiple conjugates with the same carrier protein are administered simultaneously [12].

Carrier suppression has been investigated for monovalent meningococcal conjugates [13], and there has been some work in relation to mixed meningococcal conjugates. For instance, reference 14 suggests that *Bordetella pertussis* fimbriae should be used as the carrier in order to avoid carrier suppression in multivalent conjugate vaccines, and reference 15 suggests that carrier suppression should be dealt with by using more than one type of carrier protein in the vaccine, with *H. influenzae* protein D and/or tetanus toxoid (Tt) being preferred.

It is an object of the invention to provide further vaccines that comprise conjugated capsular saccharides from multiple meningococcal serogroups but which avoid the risk of carrier-induced epitopic suppression.

DISCLOSURE OF THE INVENTION

In contrast to the approach suggested in reference 15 for avoiding carrier suppression, namely the use of more than one type of different carrier protein, the invention uses the same type of carrier protein (a 'common carrier') for multiple conjugates, which simplifies manufacture of the vaccine at a commercial scale. By choosing a common carrier, however, the potential for carrier suppression is increased. Vaccines are generally prepared by mixing individual conjugates that have been prepared in separate concentrated bulks, and each bulk will usually include a residual amount of unconjugated carrier protein from the conjugation reaction. Unconjugated carrier can give rise to carrier suppression, and if each concentrated bulk includes x amount of unconjugated carrier then a tetravalent mixture will include 4× unconjugated carrier. When carrier suppression is seen only when a particular threshold of carrier is present (e.g. only when the level of unconjugated carrier is high enough to saturate the relevant B cells and/or T cells, or only when it is high enough to stimulate the relevant T suppressor cells) then the 4× level can result in suppression even though the level of each individual conjugate is below the threshold and would not cause suppression if administered alone.

The choice of a common carrier for multivalent vaccines thus increases the carrier suppression risks significantly when compared to the monovalent vaccine or when compared to conjugates that use different carrier proteins. To compensate for this increased risk, the invention controls the amount of unconjugated carrier protein in a vaccine. Whereas the potential for carrier suppression is addressed in references 13 to 15 by focusing on the nature of the carrier protein(s) used for the meningococcal saccharides, the invention focuses instead on the amount of the carrier protein that is used, and more particularly on the amount that is present in an unconjugated form. By minimising the amount of unconjugated carrier protein in a vaccine then carrier suppression can be avoided, even where a common carrier is used.

Inclusion of unconjugated carrier protein in conjugate vaccines has been considered before [16], but the concentration of unconjugated carrier protein (tetanus toxoid) in this previous work was about 10 Lf/dose. With a 0.5 ml dose, and using a conversion factor of 1 Lf=3 µg [12], these vaccines contained about 60 µg/ml of unconjugated carrier protein. Reference 16 was not concerned with avoidance of carrier suppression.

Thus the invention provides a composition for immunising a patient against a disease caused by *Neisseria meningitidis*, comprising at least two of: (a) a conjugate of (i) the capsular saccharide of serogroup A *N. meninigitidis* and (ii) a carrier protein; (b) a conjugate of (i) the capsular saccharide of serogroup C *N. meningitidis* and (ii) a carrier protein; (c) a conjugate of (i) the capsular saccharide of serogroup W135 *N. meningitidis* and (ii) a carrier protein; (d) a conjugate of (i) the capsular saccharide of serogroup Y *N. meningitidis* and (ii) a carrier protein, characterised in that (1) at least two of said conjugates (a), (b), (c) and (d) use the same carrier protein ('the common carrier'), and (2) the composition includes the common carrier in an unconjugated form, wherein the concentration of the unconjugated common carrier is less than 10 µg/ml.

The invention also provides a process for preparing a composition for immunising a patient against a disease caused by *Neisseria meningitidis*, comprising the steps of:
(1) preparing at least two of: (a) a conjugate of (i) the capsular saccharide of serogroup A *N. meningitidis* and (ii) a carrier protein; (b) a conjugate of (i) the capsular saccharide of serogroup C *N. meningitidis* and (ii) a carrier protein; (c) a conjugate of (i) the capsular saccharide of serogroup W135 *N. meningitidis* and (ii) a carrier protein; (d) a conjugate of (i) the capsular saccharide of serogroup Y *N. meningitidis* and (ii) a carrier protein, wherein at least two of said conjugates (a), (b), (c) and (d) use the same carrier protein ('the common carrier'); and
(2) mixing the at least two conjugates prepared in (1),
to give a composition that includes the common carrier in an unconjugated form, wherein the concentration of the unconjugated common carrier is less than 10 µg/ml.

The process may include one or more steps of measuring the amount of unconjugated common carrier. Such measurements may be performed on the individual conjugates prior to mixing and/or on the combined conjugates after mixing. An individual conjugate may be rejected or selected for mixing based on the results of such measurements, and the final composition may similarly be rejected or selected for release to physicians based on the results of such measurements.

The invention also provides a process for preparing a composition for immunising a patient against a disease caused by *Neisseria meningitidis*, comprising the steps of:
(a) selecting n different meningococcal serogroups from the group consisting of A, C, W135 and Y, where the value of n is 2, 3 or 4; (b) for each of the n chosen serogroups, preparing a conjugate of (i) the capsular saccharide from that serogroup and (ii) a carrier protein, where each of the n conjugates uses the same carrier protein ('the common carrier'); and (c) mixing the n conjugates prepared in step (b), to give a composition that includes the common carrier in an unconjugated form, wherein the concentration of the unconjugated common carrier is less than 10 µg/ml. Preferably the value of n is 4, such that the invention provides a process for preparing a composition for immunising a patient against a disease caused by *Neisseria meningitidis*, comprising the steps of: (a) preparing for each of meningococcal serogroups A, C, W135 and Y a conjugate of (i) the capsular saccharide from that serogroup and (ii) a carrier protein, where each of the four conjugates uses the same carrier protein; and (b) mixing the conjugates to give a composition that includes the common carrier in an unconjugated form, wherein the concentration of the unconjugated common carrier is less than 10 µg/ml.

As before, this process may include one or more steps of measuring the amount of unconjugated common carrier, before and/or after mixing in step (b).

The Conjugates

Conjugation is used to enhance the immunogenicity of saccharides, as it converts them from T-independent antigens to T-dependent antigens, thus allowing priming for immunological memory. Conjugation is particularly useful for pediatric vaccines [e.g. ref. 17] and is a well known technique [e.g. reviewed in refs. 18 to 27].

The composition of the invention includes at least two (i.e. 2, 3 or 4) of the following meningococcal conjugates:

(a) conjugate of (i) the capsular saccharide of serogroup A *N. meningitidis* and (ii) a carrier protein; (b) a conjugate of (i) the capsular saccharide of serogroup C *N. meningitidis* and (ii) a carrier protein; (c) a conjugate of (i) the capsular saccharide of serogroup W135 *N. meningitidis* and (ii) a carrier protein; (d) a conjugate of (i) the capsular saccharide of serogroup Y *N. meningitidis* and (ii) a carrier protein.

Of these conjugates, at least two (i.e. 2, 3 or 4) use a common carrier protein. This does not mean that a single conjugate molecule includes saccharides from more than one serogroup (cf. references 28 & 29). Rather, a single conjugate molecule carries saccharide from a single serogroup, but the same type of carrier protein is used for each different serogroup. Within a single conjugate molecule, however, there may be more than one type of saccharide (e.g. different length fragments), but these will be derived from a single serogroup. As an example of using a common carrier, a sample of protein may be split into quarters, with each quarter then being used to prepare a conjugate using capsular saccharide fragments from for a single serogroup, and the conjugates may then be mixed to give a tetravalent conjugate with a common carrier.

The capsular saccharides are chosen from meningococcal serogroups A, C, W135 and Y, such that the compositions include saccharides from 2, 3, or all 4 of these four serogroups. Specific compositions comprise saccharides from: serogroups A & C; serogroups A & W135; serogroups A & Y; serogroups C & W135; serogroups C & Y; serogroups W135 & Y; serogroups A & C & W135; serogroups A & C & Y; serogroups A & W135 & Y; serogroups C & W135 & Y; serogroups A & C & W135 & Y. Compositions including at least serogroup C are preferred (e.g. A & C), and compositions including saccharides from all four serogroups are most preferred.

The capsular saccharides of each of these four serogroups are well characterised. The capsular saccharide of serogroup A meningococcus is a homopolymer of ($\alpha$1→6)-linked N-acetyl-D-mannosamine-1-phosphate, with partial O-acetylation in the C3 and C4 positions. The acetyl groups can be replaced with blocking groups to prevent hydrolysis [30], and such modified saccharides are still serogroup A saccharides within the meaning of the present invention. The serogroup C capsular saccharide is a homopolymer of ($\alpha$2→9)-linked sialic acid (N-acetyl neuraminic acid, or 'NeuNAc'). Most serogroup C strains have O-acetyl groups at C-7 and/or C-8 of the sialic acid residues, but about 15% of clinical isolates lack these O-acetyl groups [31,32]. The saccharide structure is written as →9)-Neu p NAc 7/8 OAc-($\alpha$2→. The serogroup W135 saccharide is a polymer of sialic acid-galactose disaccharide units. Like the serogroup C saccharide, it has variable O-acetylation, but at sialic acid 7 and 9 positions [33]. The structure is written as: →4)-D-Neup5Ac(7/9OAc)-$\alpha$-(2→6)-D-Gal-$\alpha$-(1→. The serogroup Y saccharide is similar to the serogroup W135 saccharide, except that the disaccharide repeating unit includes glucose instead of galactose. Like serogroup W135, it has variable O-acetylation at sialic acid 7 and 9 positions [33]. The serogroup Y structure is written as: →4)-D-Neup5Ac(7/9OAc)-$\alpha$-(2→6)-D-Glc-$\alpha$-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides.

The saccharides used according to the invention are preferably shorter than the native capsular saccharides seen in bacteria. Thus the saccharides are preferably depolymerised, with depolymerisation occurring after purification but before conjugation. Depolymerisation reduces the chain length of the saccharides. A preferred depolymerisation method involves the use of hydrogen peroxide [7]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [8], with preferred depolymerised saccharides in conjugates of the invention having the following range of average degrees of polymerisation: A=10-20; C=12-22; W135=15-25; Y=15-25. Other depolymerisation methods are known to the skilled person. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides.

Typical carrier proteins for use in conjugates are bacterial toxins, such as diphtheria toxin [e.g. see chapter 13 of ref. 34; refs. 35-38] (or its CRM197 mutant [39-42]) and tetanus toxin, usually in toxoid form (e.g. obtained by treatment with an inactivating chemical, such as formalin or formaldehyde). Other suitable carrier proteins include *N. meningitidis* outer membrane protein [43], synthetic peptides [44,45], heat shock proteins [46, 47], pertussis proteins [48, 49], cytokines [50], lymphokines [50], hormones [50], growth factors [50], artificial proteins comprising multiple human CD4$^+$ T cell epitopes from various pathogen-derived antigens [51], protein D from *H. influenzae* [52-54], pneumolysin [55], pneumococcal surface protein PspA [56], iron-uptake proteins [57], toxin A or B from *C. difficile* [58], etc.

Four particularly preferred carrier proteins for use as common carriers are diphtheria toxoid (Dt), tetanus toxoid (Tt), CRM197 and protein D from *H. influenzae*. These proteins are preferred because they are the main carriers currently in use in pediatric vaccines and so they are the carriers most at risk of carrier suppression e.g. from earlier, concurrent or later administration of other vaccines. Dt and protein D are the most preferred common carriers, as these proteins are used in existing pediatric vaccines less frequently than CRM197 and Tt e.g. the Hib conjugates from GSK use Tt as the carrier, the HibTITER™ product uses CRM197, the pneumococcal conjugates in Prevenar™ use CRM197, the Menjugate™ and Meningitec™ products use CRM197, and NeisVac-C™ uses Tt. To further minimise the risk of carrier suppression, therefore, Dt and *H. influenzae* protein D are used as common carriers.

Conjugates are preferably mixed to give substantially a 1:1:1:1 ratio (measured as mass of saccharide) e.g. the mass of each serogroup's saccharide is within ±10% of each other. A typical quantity of meningococcal antigen per serogroup in a composition is between 1 μg and 20 μg e.g. between 2 and 10 μg per serogroup, or about 4 μg. As an alternative to a 1:1:1:1 ratio, a double serogroup A dose may be used (2:1:1:1).

Conjugates with a saccharide:protein ratio (w/w) of between 1:15 (i.e. excess protein) and 15:1 (i.e. excess saccharide), preferably between 1:5 and 5:1, are preferred. Excess carrier protein is preferred. Conjugates with saccharide:protein ratio of about 1:12 or about 1:3 are preferred, particularly where the carrier is Dt.

Any suitable conjugation reaction can be used, with any suitable linker where necessary.

The saccharide will typically be activated or functionalised prior to conjugation. Activation may involve, for example, cyanylating reagents [59, 60, etc.]). Other suitable techniques use active esters, carbodiimides, hydrazides, norborane, p-nitrobenzoic acid, N-hydroxysuccinimide, S-NHS, EDC, TSTU; see also the introduction to reference 24).

Linkages via a linker group may be made using any known procedure, for example, the procedures described in references 61 and 62. One type of linkage involves reductive amination of the polysaccharide, coupling the resulting amino group with one end of an adipic acid linker group, and then coupling a protein to the other end of the adipic acid linker group [22, 63, 64]. Other linkers include B-propionamido [65], nitrophenyl-ethylamine [66], haloacyl halides [67], glycosidic linkages [68], 6-aminocaproic acid [69], ADH [70], $C_4$ to $C_{12}$ moieties [71] etc. As an alternative to using a linker, direct linkage can be used. Direct linkages to the protein may comprise oxidation of the polysaccharide followed by reductive amination with the protein, as described in, for example, references 72 and 73.

A preferred conjugation process involves: introduction of amino groups into the saccharide (e.g. by replacing terminal =O groups with —NH$_2$) followed by derivatisation with an adipic diester (e.g. adipic acid N-hydroxysuccinimide diester) and reaction with carrier protein (e.g. CRM197). Further details of this conjugation method can be found in reference 8. Conjugates obtainable by this method are preferred conjugates for use according to the invention.

In another preferred conjugation process, a saccharide is reacted with adipic acid dihydrazide. For serogroup A, carbodiimide (EDAC) may also be added at this stage. After a reaction period, sodium cyanoborohydride is added. Derivatised saccharide can then be prepared e.g. by ultrafiltration. The derivatized saccharide is then mixed with carrier protein (e.g. with a diphtheria toxoid), and carbodiimide is added. After a reaction period, the conjugate can be recovered. Further details of this conjugation method can be found in reference 8. Conjugates obtainable by this method are preferred conjugates for use according to the invention e.g. conjugates comprising a diphtheria toxoid carrier and an adipic acid linker.

In another preferred conjugation process, a saccharide is derivatised with a cyanylating reagent [60], followed by coupling to a protein (direct, or after introduction of a thiol or hydrazide nucleophile group into the carrier), without the need to use a linker. Suitable cyanylating reagents include 1-cyano-4-(dimethylamino)-pyridinium tetrafluoroborate ('CDAP'), p-nitrophenylcyanate and N-cyanotriethylammonium tetrafluoroborate ('CTEA'). CDAP is preferred, particularly where *H. influenzae* protein D is the common carrier. Direct coupling is preferred.

Conjugates are preferably prepared separately and then mixed. After mixing, the concentration of the mixed conjugates can be adjusted e.g. with sterile pyrogen-free, phosphate-buffered saline.

In addition to the common carrier, conjugates with other carrier proteins may be present in compositions of the invention. In general, however, it is preferred that all meningococcal conjugates in the composition use the same common carrier.

In compositions of the invention, the amount of carrier (conjugated and unconjugated) from each conjugate is preferably no more than 100 μg/ml e.g. <30 μg/ml of carrier protein from each conjugate. Preferred compositions include a total concentration of common carrier (either solely for the combined meningococcal conjugates, or preferably for the composition as a whole) of less than 500 μg/ml e.g. less than 400 μg/ml, less than 300 μg/ml, less than 200 μg/ml, less than 100 μg/ml, less than 50 μg/ml, etc.

Unconjugated Common Carrier Protein

Compositions of the invention include the common carrier in an unconjugated form, but the unconjugated common carrier is present at less than 10 μg/ml.

By control of factors such as conjugation conditions, post-conjugation purification, post-conjugation storage conditions (temperature, pH, moisture, etc.) then it is possible, according to the invention, to ensure that the amount of unconjugated common carrier is reliably kept below 10 μg/ml, and can typically be kept even lower e.g. below 9 μg/ml, below 8 μg/ml, below 7 μg/ml, below 6 μg/ml, below 5 μg/ml, below 4 μg/ml, below 3 μg/ml, below 2 μg/ml, below 1 μg/ml, below 0.5 μg/ml, etc.

For practical reasons, however, it is advantageous to include a low level of unconjugated common carrier, in order to provide a slight adjuvant effect without leading to carrier suppression problems. The concentration of unconjugated common carrier in the composition of the invention is thus preferably ≥a μg/ml but <b μg/ml, where b>a and where: (i) a is selected from the group consisting of 0.01, 0.05, 0.1, 0.2, 0.3, 0.4, 0.5, 0.6, 0.7, 0.8, 0.9, 1, 2, 3, 4 and 5; and (ii) b is selected from the group consisting of 0.5, 0.6, 0.7, 0.8, 0.9, 1, 2, 3, 4, 5, 6, 7, 8, 9 and 10.

The unconjugated carrier in the compositions of the invention has two origins. First, it may come from the individual conjugates that are mixed. The individual conjugates may include unreacted residual carrier from the conjugation reaction, and may include carrier that has been released by breakdown of conjugated material. Second, it can come from breakdown of conjugates after mixing e.g. after storage of the composition. Unconjugated carrier will not normally be added on purpose as a separate step during manufacture. The concentration of unconjugated common carrier in a composition can thus increase over time. Preferred compositions are those with <10 μg/ml unconjugated common carrier when measured 6 hours after all meningococcal conjugates have been mixed. Other preferred compositions are those which have <10 μg/ml unconjugated common carrier throughout a period of at least 1 month (e.g. 2 month, 3 months, 6 months, or longer) starting from the time of first conjugate mixing.

In the processes of the invention, the conjugates that are mixed can include unconjugated common carrier, and the unconjugated carrier present after mixing will be carried through from the component conjugates. If composition of the invention includes a total of x μg of unconjugated common carrier from meningococcal conjugates and n different meningococcal conjugates then, on average, each conjugate will have contributed x/n μg of unconjugated common carrier. In preferred processes of the invention, where the composition includes a total of x μg of unconjugated common carrier from the meningococcal conjugates then the amount of each of the n individual meningococcal conjugates is selected to provide an amount of unconjugated common carrier within ±15% of x/n, for example ±10%, ±7.5% or ±5%. In concentration terms, each individual conjugate preferably contributes less than 2 μg/ml of unconjugated carrier.

The unconjugated common carrier in a composition may be present in solution, it may be present as a precipitate, or it may be adsorbed to any adjuvant that may be present.

Levels of unconjugated carrier can be measured using standard and known methods e.g. those previously used for assessing unconjugated carrier in Hib conjugate vaccines.

To compare levels of unconjugated carrier to total carrier (or to conjugated carrier) then it is generally necessary to separate the unconjugated carrier from conjugated carrier such that it can be assayed separately. As the conjugated carrier is larger than the unconjugated carrier then one way of achieving this is to separate by size e.g. by size exclusion chromatography, by electrophoresis, etc. Approximate MWs of typical carriers (in monomeric form) are: CRM197=58 kDa; Dt=63 kDa; Tt=150 kDa; protein D=42 kDa.

One method of measuring the level of unconjugated carrier comprises a step of electrophoretic separation, with the level of unconjugated carrier being compared to one or more standards containing a known amount of the carrier. After protein quantification (e.g. by staining, such as by silver staining) then the amount relative to the standard(s) can be determined. A third analysis can also be run in parallel, where a sample of the unconjugated carrier is mixed with the standard, with this mixture also being compared to the previous two bands.

Other methods for measuring unconjugated carrier protein may involve capillary electrophoresis [74] (e.g. in free solution), or micellar electrokinetic chromatography [75], particularly where the common carrier is a diphtheria toxoid. Resolution of the conjugate and the carrier can be improved by increasing borate concentration during analysis.

Assays to measure unconjugated carrier levels can be performed at various stages during processes of the invention. For example, they can be performed on one or more of the individual conjugates before they are mixed, and/or they can be performed after mixing. The invention requires a composition to include less than 10 μg/ml unconjugated common meningococcal carrier, as described above, and this level can be verified by performing the assay after mixing. As an alternative to assaying after mixing, however, the assay can be performed on the individual conjugates before mixing, with the individual results then being used to calculate the final level (taking into account any dilutions, etc.), provided that conditions are used in mixing that are known not to cause an increase in unconjugated carrier.

With the measurement assays and a maximum permitted amount of unconjugated carrier protein (e.g. 10 μg/ml, as mentioned above), the skilled person can check whether any particular composition falls within the scope of the invention. Moreover, the skilled person can accept or reject (a) an individual conjugate prior to mixing and/or (b) combined conjugates after mixing, based on whether the level of unconjugated carrier protein is above or below the maximum permitted amount. Thus the invention provides a process for preparing a composition, comprising the mixing steps defined above, and further comprising the step of: measuring the concentration of unconjugated common carrier in the composition; and either (i) if the concentration of unconjugated carrier is <10 μg/ml, accepting the composition for further vaccine manufacture, and/or for administration to humans; or (ii) if the concentration of unconjugated carrier is ≥10 μg/ml, rejecting the composition.

As well as including only small amounts of common carrier, preferred compositions of the invention similarly include only small amounts of unconjugated meningococcal capsular saccharides. Thus the composition preferably includes no more than 2 μg/ml (measured as saccharide) unconjugated saccharide e.g. <1.5 μg/ml, <1 μg/ml, <0.5 μg/ml, etc.

The Composition

As well as comprising meningococcal conjugates and unconjugated carrier protein, compositions of the invention will typically include a pharmaceutically acceptable carrier. Such carriers include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable carriers and excipients is available in reference 76.

Compositions used according to the invention may include an antimicrobial, particularly if packaged in a multiple dose format.

Compositions used according to the invention may comprise detergent e.g. a Tween (polysorbate), such as Tween 80. Detergents are generally present at low levels e.g. <0.01%.

Compositions used according to the invention may include sodium salts (e.g. sodium chloride) to give tonicity. A concentration of 10±2 mg/ml NaCl is typical.

Compositions used according to the invention will generally include a buffer e.g. a phosphate buffer.

Bacterial infections can affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 77 & 78]. In general, however, the meningococcal conjugates are formulated for intramuscular injection.

Compositions used according to the invention may or may not include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 79], or mixtures of different mineral compounds, with the compounds taking any suitable form (e.g. gel, crystalline, amorphous, etc.). The mineral containing compositions may also be formulated as a particle of metal salt [80].

Aluminium phosphates are particularly preferred, and a typical adjuvant is amorphous aluminium hydroxyphosphate with $PO_4$/Al molar ratio between 0.84 and 0.92, included at about 0.6 mg $Al^{3+}$/ml. Adsorption with a low dose of aluminium phosphate may be used e.g. between 50 and 100 µg $Al^{3+}$ per conjugate per dose.

Conjugates may or may not be adsorbed (or may be partially adsorbed) to any aluminium salt that is present. Where a composition includes conjugates from multiple bacterial species then not all conjugates need to be adsorbed.

B. Oil Emulsions

Oil emulsion compositions suitable for use as adjuvants in the invention include squalene-water emulsions, such as MF59 [Chapter 10 of ref. 79; see also ref. 81] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 79]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 82. Saponin formulations may also comprise a sterol, such as cholesterol [83].

Combinations of saponins and cholesterols can be used to form unique particles called immunostimulating complexs (ISCOMS) [chapter 23 of ref. 79]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 83-85. Optionally, the ISCOMS may be devoid of additional detergent [86].

A review of the development of saponin based adjuvants can be found in refs. 87 & 88.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 89-94. Virosomes are discussed further in, for example, ref. 95.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 96. Such "small particles" of 3dMPL are small enough to be sterile filtered through a 0.22 µm membrane [96]. Other non-toxic LPS derivatives include monophosphoryl lipid A mimics, such as aminoalkyl glucosaininide phosphate derivatives e.g. RC-529 [97,98].

Lipid A derivatives include derivatives of lipid A from *Escherichia coli* such as OM-174. OM-174 is described for example in refs. 99 & 100.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 101, 102 and 103 disclose possible analog substitutions e.g. replacement of guanosine with 2'-deoxy-7-deazaguanosine. The adjuvant effect of CpG oligonucleotides is further discussed in refs. 104-109.

The CpG sequence may be directed to TLR9, such as the motif GTCGTT or TTCGTT [110]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 111-113. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 110 & 114-116.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 117 and as parenteral adjuvants in ref. 118. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 119-126. Numerical reference for amino acid substitutions is preferably based on the alignments of the A and B subunits of ADP-ribosylating toxins set forth in ref. 127, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [128], etc.) [129], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [130] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [131].

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 79)

Examples of liposome formulations suitable for use as adjuvants are described in refs. 132-134.

J. Polyoxyethylene Ether and Polyoxyethylene Ester Formulations

Adjuvants suitable for use in the invention include polyoxyethylene ethers and polyoxyethylene esters [135]. Such formulations further include polyoxyethylene sorbitan ester surfactants in combination with an octoxynol [136] as well as polyoxyethylene alkyl ethers or ester surfactants in combination with at least one additional non-ionic surfactant such as an octoxynol [137]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 138 and 139.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e,g. "Resiquimod 3M"), described further in refs. 140 and 141.

The invention may also comprise combinations of aspects of one or more of the adjuvants identified above. For example, the following adjuvant compositions may be used in the invention: (1) a saponin and an oil-in-water emulsion [142]; (2) a saponin (e.g. QS21)+a non-toxic LPS derivative (e.g. 3dMPL) [143]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [144]; (5) combinations of 3dMPL with, for example, QS21 and/or oil-in-water emulsions [145]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (DetoX™); and (8) one or more mineral salts (such as an aluminum salt)+a non-toxic derivative of LPS (such as 3dMPL).

Other substances that act as immunostimulating agents are disclosed in chapter 7 of ref. 79.

The use of an aluminium hydroxide or aluminium phosphate adjuvant is particularly preferred [e.g. examples 7 & 8 of ref. 7; example J of ref. 8], with or without adsorption. A composition with no aluminium salt adjuvant can also be used [ref. 15]. Calcium phosphate is another preferred adjuvant. Conjugates may be mixed with (and optionally adsorbed to) the adjuvants separately and then the conjugates may be mixed together, or the conjugates may be mixed together and then mixed with adjuvant.

The pH of compositions used according to the invention is preferably between 6 and 8, preferably about 7. Stable pH may be maintained by the use of a buffer. Where a composition comprises an aluminium hydroxide salt, it is preferred to use a histidine buffer [146]. The composition may be sterile and/or pyrogen-free. Compositions may be isotonic with respect to humans.

Compositions may include a preservative (e.g. thiomersal, 2-phenoxyethanol), or may be preservative free. Preferred compositions of the invention do not include any mercurial material e.g. they are thiomersal-free.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Compositions will comprise an immunologically effective amount of the meningococcal conjugates, as well as any other components, as needed. By 'immunologically effective amount', it is meant that the administration of that amount to an individual, either in a single dose or as part of a series, elicits a protective anti-meningococcal immune response in patients. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal antigen per dose is between 1 µg and 20 µg per serogroup (measured in terms of saccharide) e.g. between 2 and 10 µg per serogroup, or between 3 and 8 µg per serogroup. A dose of about 4 µg per serogroup is preferred (i.e. a total of 16 µg in a tetravalent mixture), or of about 5 µg per serogroup (i.e. a total of 20 µg in a tetravalent mixture).

Lyophilisation

Vaccines are typically administered by injection, particularly intramuscular injection. Compositions of the invention are generally presented at the time of use as aqueous solutions or suspensions. In some embodiments of the invention the compositions are in aqueous form from the packaging stage to the administration stage ('full liquid' vaccine). In other embodiments, however, one or more components of the compositions may be packaged in a lyophilised form, and a vaccine for actual administration may be reconstituted when necessary. Thus compositions of the invention may be prepared at a packaging stage, or may be prepared extemporaneously prior to use. Lyophilisation of meningococcal conjugates is known in the art e.g. the Menjugate™ product is presented in lyophilised form, whereas NeisVac-C™ and Meningitec™ are full liquid vaccines.

In some embodiments, therefore, the compositions of the invention are in lyophilised form. Individual meningococcal conjugates may be lyophilised prior to mixing, or may be mixed in aqueous form and then be lyophilised.

The invention also provides a kit for preparing a composition of the invention, wherein the kit comprises at least one meningococcal conjugate in lyophilised form and at least one meningococcal conjugate in aqueous form. The kit may comprise two vials (one containing aqueous material and one containing lyophilised material), or it may comprise one ready-filled syringe and one vial e.g. with the contents of the syringe being used to reconstitute the contents of the vial prior to injection. For compositions that include a serogroup A conjugate then the serogroup A saccharide may be lyophilised, whereas conjugate(s) from other serogroup(s) may be present in liquid form.

The invention also provides a kit for preparing an aqueous composition of the invention, wherein the kit comprises (i) a lyophilised composition of the invention, and (ii) aqueous material, wherein component (ii) is for reconstituting component (i) in order to provide the aqueous composition. Component (ii) is preferably sterile, non-pyrogenic, etc., as described above.

Thus the invention encompasses compositions in fully-lyophilised form, fully-aqueous form, and in a form ready for reconstitution to give an aqueous formulation.

To stabilise conjugates during lyophilisation, it is preferred to include a sugar alcohol (e.g. mannitol) or a disaccharide (e.g. sucrose or trehalose) e.g. at between 1 mg/ml and 30 mg/ml (e.g. about 25 mg/ml) in the composition. Lyophilisation in the presence of sucrose is preferred. Compositions of the invention may thus include a sugar alcohol or a disaccharide, particularly where they are either in lyophilised form or have been reconstituted from lyophilised material.

Where a composition is in lyophilised form (or includes a lyophilised component) then the lyophilised material preferably does not include an aluminium adjuvant. If a final aqueous composition with an aluminium adjuvant is desired then the adjuvant should instead be present in the material used to reconstitute the lyophilised material (cf. Menjugate™).

The Patient

Compositions of the invention are for protecting patients against meningococcal disease e.g. against meningitis, more preferably bacterial meningitis, and most preferably meningococcal meningitis.

The patient to be immunised will typically be a human. The human will generally be at least 1 month old e.g. at least 2 months old, at least 4 months old, at least 6 months old, at least 2 years old, at least 5 years old, at least 11 years old, at least 17 years old, at least 40 years old, at least 55 years old, etc. A preferred set of patients is in the age group 2-55 years old, and another preferred set of patients is in the age group 11-55 years old. A further preferred set of patients is less than 11 years old e.g. 2-11 years old. A further preferred set of patients is less than 2 years old e.g. less than 1 year old. The compositions of the invention are particularly useful for immunising patients who have already received the common carrier protein in a previous immunisation.

Before or at substantially the same time as receiving the composition of the invention, the patient may be immunised with one or more further vaccines. Other vaccines that may have been or may be administered include, but are not limited to: diphtheria antigens, such as a diphtheria toxoid; tetanus antigens, such as a tetanus toxoid; pertussis antigen (s), such as a whole cell/cellular pertussis vaccine ('Pw') or, preferably, an acellular pertussis vaccine ('Pa'); *Haemophilus influenzae* type B capsular saccharide, typically conjugated; hepatitis B surface antigen (HBsAg); poliovirus, such as an inactivated poliovirus vaccine (IPV) or an oral poliovirus vaccine (OPV); *Streptococcus pneumoniae* capsular saccharide, typically multivalent and conjugated; influenza virus; BCG; hepatitis A virus antigens; measles virus; mumps virus; rubella virus; vadricella virus; etc. Further details on some of these further vaccines are given below.

The result of administering a composition of the invention is preferably that, for each administered serogroup, the patient raises a serum bactericidal antibody (SBA) response, with the increase in SBA titre (compared to the pre-immunised patient before receiving the composition) being at least 4-fold, and preferably at least 8-fold. The SBA test is a standard correlate for meningococcal protection. Further details of serologic correlates for meningococcal vaccines are given in reference 147.

Further Antigenic Components of Compositions Used According to the Invention

Compositions of the invention can be used for immunising patients against meningococcal disease and can be used separately from other vaccination components. In addition, however, compositions of the invention may be used in conjunction with other vaccine components. These other components may be administered separately from the compositions of the invention, but at substantially the same time, or the compositions of the invention may include these further components as part of a combination vaccine.

In addition to meningococcal conjugate antigens, therefore, compositions of to the invention may optionally include one or more of the following further antigens:

1. A conjugated capsular saccharide from *H. influenzae* type B ('Hib') [e.g. chapter 14 of ref. 34]. The carrier protein for the conjugate may be CRM197, a diphtheria toxoid, a tetanus toxoid or an outer membrane complex of *N. meningitidis*. The saccharide moiety of the conjugate may be a polysaccharide (e.g. full-length polyribosylribitol phosphate (PRP)), but it is preferred to depolymerise the capsular polysaccharides to form oligosaccharides (e.g. MW from ~1 to ~5 kDa). A preferred Hib conjugate comprises an oligosaccharide covalently linked to CRM197 via an adipic acid linker [148, 149]. Administration of the Hib antigen to a patient preferably results in an anti-PRP antibody concentration of >0.15 µg/ml, and more preferably >1 µg/ml. Where a composition includes a Hib saccharide antigen, it preferably does not also include an aluminium hydroxide adjuvant. If the composition includes an aluminium phosphate adjuvant then the Hib antigen may be adsorbed to the adjuvant [150] or it may be non-adsorbed [15]. Prevention of adsorption can be achieved by selecting the correct pH during antigen/adjuvant mixing, an adjuvant with an appropriate point of zero charge, and an appropriate order of mixing for the various different antigens in a composition [151].

2. A conjugated capsular saccharide from *S. pneumoniae* [e.g. chapter 23 of ref. 34; refs. 152-154]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [155]. For example, PrevNar™ [156] contains antigens from seven serotypes (4, 6B, 9V, 14, 18C, 19F, and 23F) with each saccharide individually conjugated to CRM197 by reductive amination, with 2 µg of each saccharide per 0.5 ml dose (4 µg of serotype 6B), and with conjugates adsorbed on an aluminium phosphate adjuvant. Where pneumococcal conjugates are included in a compositions for use with the invention, the composition preferably includes at least serotypes 6B, 14, 19F and 23F.

3. A protein antigen from *Neisseria meningitidis* serogroup B [e.g. ref 157].

4. A diphtheria antigen, such as a diphtheria toxoid [e.g. chapter 13 of ref. 34].

5. A tetanus antigen, such as a tetanus toxoid [e.g. chapter 27 of ref. 34].

6. A cellular or whole cell pertussis ('Pw') antigen [e.g. chapter 21 of ref. 34].

7. One or more acellular pertussis ('Pa') antigens [e.g. chapter 21 of ref. 34].

A Pa component will generally include one, two or three of the following well-characterised *B. pertussis* antigens: (1) pertussis toxoid ('PT'), detoxified either by chemical means or by site-directed mutagenesis e.g. the '9K/129G' mutant [158]; (2) filamentous haemagglutinin ('FHA'); (3) pertactin (also known as '69 kiloDalton outer membrane protein'). A Pa component may also include agglutinogen 2 and/or agglutinogen 3.

8. An antigen from hepatitis B virus, such as the surface ('HBsAg') and/or core antigens [e.g. refs. 159 & 164; chapter 16 of ref. 34], with surface antigen preferably being adsorbed onto an aluminium phosphate [160].

9. One or more poliovirus antigen(s) [e.g. 161, 162; chapter 24 of ref. 34] such as IPV. Inclusion of Mahoney strain, MEF-1 strain and Saukett strain is normal.

10. An antigen from hepatitis A virus, such as inactivated virus [e.g. 163, 164; chapter 15 of ref. 34].

The composition may include one or more (i.e. 1, 2, 3, 4, 5, 6, 7, 8, 9 or 10) of these further antigens. In other embodiments, the composition may specifically not include one or more of these further antigens.

Where present, these further antigens may or may not be adsorbed to an aluminium salt.

Where a diphtheria antigen is included in the mixture it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the mixture will typically be present at a concentration of at least 1 µg/ml each. In general, the concentration of any given antigen will be sufficient to elicit an immune response against that antigen. It is preferred that the protective efficacy of individual saccharide antigens is not removed by combining them, although actual immunogenicity (e.g. ELISA titres) may be reduced.

If meningococcal conjugates are being administered in a series of doses then none, some or all of the doses may include these extra antigens.

As an alternative to the compositions including one or more of these 10 additional components, the invention provides a kit comprising: (i) a composition of the invention, either in aqueous or lyophilised form; and (ii) a composition comprising one or more of these 10 additional components. Where component (i) is lyophilised then component (ii) is preferably in aqueous form and can be used to reconstitute (i).

Thus compositions of the invention may be sold for use on their own, may be sold for use in conjunction with other vaccine materials, or may be sold as part of a vaccination kit.

Medical Treatments

The invention provides a method for treating a patient, comprising administering to the patient an immunologically effective amount of a composition of the invention. The patient may either be at risk from the disease themselves or may be a pregnant woman ('maternal immunisation').

The invention also provides a composition of the invention, for use as a medicament (e.g. as an immunogenic composition or as a vaccine).

The invention also provides the use of at least two of: (a) a conjugate of (i) the capsular saccharide of serogroup A *N. meningitidis* and (ii) a carrier protein; (b) a conjugate of (i) the capsular saccharide of serogroup C *N. meningitidis* and (ii) a carrier protein; (c) a conjugate of (i) the capsular saccharide of serogroup W135 *N. meningitidis* and (ii) a carrier protein; (d) a conjugate of (i) the capsular saccharide of serogroup Y *N. meningitidis* and (ii) a carrier protein, in the manufacture of a medicament for immunising a patient against a disease caused by *Neisseria meningitidis*, characterised in that (1) at least two of said conjugates (a), (b), (c) and (d) use the same carrier protein ('the common carrier'), and (2) the medicament includes the common carrier in an unconjugated form at a concentration of less than 10 μg/ml.

Where a vaccine is for prophylactic use, the patient is preferably a child (e.g. a toddler or infant); where the vaccine is for therapeutic use, the patient is preferably an adult. A vaccine intended for children may also be administered to adults e.g. to assess safety, dosage, immunogenicity, etc.

One way of checking efficacy of therapeutic treatment involves monitoring meningococcal infection after administration of the composition of the invention. One way of checking efficacy of prophylactic treatment involves monitoring immune responses against an administered polypeptide after administration. Immunogenicity of compositions of the invention can be determined by administering them to test subjects, and serologic correlates for meningococcal vaccines are given in reference 147.

Compositions will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration (e.g. to the thigh or the upper arm) is preferred. Injection may be via a needle (e.g. a hypodermic needle), but needle-free injection may alternatively be used. A typical intramuscular dose is 0.5 ml.

Meningococcal conjugates from multiple serogroups are administered in admixture within a single composition. The composition may be administered as a single dose, or may be administered more than once in a multiple dose schedule. Multiple doses may be used in a primary immunisation schedule and/or in a booster immunisation schedule. A primary dose schedule may be followed by a booster dose schedule of the meningococcal conjugates. Suitable timing between priming doses (e.g. between 4-16 weeks), and between priming and boosting, can be routinely determined. The invention may be used to elicit systemic and/or mucosal immunity.

Specific Compositions of the Invention

Preferred embodiments of the invention include:

1. An aqueous composition comprising meningococcal conjugates from serogroups C, W135 and Y, with a CRM197 carrier for each. The saccharides are linked to the carrier using an adipic acid linker. The concentration of unconjugated CRM197 is <5 μg/ml. The concentration of each conjugate (measured as saccharide) is about 10 μg/ml. The composition includes an aluminium phosphate adjuvant, with no step of adsorption to the adjuvant during preparation. The composition includes sodium chloride, sodium phosphate (monobasic & dibasic, for buffering) and small amounts of polysorbate 80. The composition is for intramuscular injection, or may be used to reconstitute a lyophilised serogroup A conjugate.

2. The aqueous composition arising from reconstitution of a lyophilised serogroup A conjugate with the composition of embodiment 1 above. The serogroup A conjugate also has a CRM197 carrier. After reconstitution, the serogroup A conjugate may be present at about 10 μg/ml or about 20 μg/ml (depending on dilution factor). After reconstitution, the concentration of unconjugated CRM197 remains <5 μg/ml.

3. An aqueous composition comprising meningococcal conjugates from serogroups A and C, with an *H. influenzae* protein D carrier for both, and with the saccharides linked to the carrier using CDAP chemistry. The concentration of unconjugated protein D is <10 μg/ml. The composition also includes an *H. influenzae* type b conjugate, with the Hib saccharide being conjugated to a tetanus toxoid carrier protein. The concentration of each of the three conjugates (measured as saccharide) is about 10 μg/ml. The composition includes no aluminium salt adjuvant. The composition includes sucrose. The pH of the composition is between 6 and 6.5 e.g. about 6.1. The composition is for lyophilisation.

4. A lyophilised composition comprising meningococcal conjugates from serogroups A and C, with a *H. influenzae* protein D carrier for both, and with the saccharides linked to the carrier using CDAP chemistry. The concentration of unconjugated protein D is <10 μg/ml. The composition also includes a *H. influenzae* type b conjugate, with the Hib saccharide being conjugated to a tetanus toxoid carrier protein. The composition includes no aluminium salt adjuvant. The composition includes sucrose. The composition reconstituted with other vaccine components, particularly non-meningococcal vaccine components.

5. The aqueous composition arising from reconstitution of the composition of embodiment 4 above with a vaccine composition comprising diphtheria, tetanus and pertussis antigens, and optionally further comprising HBsAg. The reconstituting vaccine will include aluminium hydroxide and/or phosphate adjuvants.

6. An aqueous composition comprising meningococcal conjugates from serogroups A, C, W135 and Y, with a diphtheria toxoid carrier for each. The saccharides may be linked to the carrier using an adipic acid linker. The concentration of unconjugated Dt is <5 μg/ml. The concentration of each conjugate (measured as saccharide) is about 8 μg/ml. The composition includes no aluminium salts. The composition is for intramuscular injection.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Concentrations of common carrier are given above in the units of "μg/ml" (micrograms per milliliter) but, in an alternative and parallel set of definitions, these μg/ml concentrations may be replaced by concentrations measured in the units "Lf/ml" (flocculation units, or the "limit of flocculation" [165]), which is a functional unit for quantifying tetanus and diphtheria toxoids. Numerical values will be divided by 3 (i.e. 3 μg/ml would become 1 Lf/ml) and, where necessary, rounded up to the nearest integer (i.e. 10 μg/ml would become 4 Lf/ml) in this alternative set of definitions. This alternative is given here purely for reasons of convenience, and should not have any influence on the invention when carrier concentrations are given in μg/ml.

MODES FOR CARRYING OUT THE INVENTION

Reduction in Anti-Serogroup C Response in Presence of Unconjugated Carrier Protein NeisVac-C™ includes serogroup C (OAc⁻) capsular saccharide conjugated to a tetanus toxoid carrier, with an aluminium hydroxide adjuvant, and with a protein:saccharide weight ratio of ~2:1. This vaccine was administered to children aged 3-6 or 13-18, either alone or with simultaneous administration of unconjugated tetanus and diphtheria toxoids, as described in reference 13. Specific IgG GMCs were measured by OAc⁺ ELISA, by OAc⁻ ELISA, and by high-avidity ELISA, and rSBA GMTs were also measured (against strain C11) [13]. Results in the two groups of patients were as follows, relative to results in patients who did not receive the Tt/Dt vaccine at the same time:

| Extra Tt | OAc⁺ ELISA GMC | OAc⁻ ELISA GMC | OAc⁺ hi-av ELISA GMC | RSBA GMT |
|---|---|---|---|---|
| − | 100% | 100% | 100% | 100% |
| + | 82% | 62% | 51% | 50% |

The effect of unconjugated Tt on the immune response is clear from these results. To avoid this effect in vaccines comprising more than one meningococcal conjugate then, according to the invention, the level of unconjugated carrier is kept below a threshold level.

Combined Meningococcal Conjugates

Mixtures of meningococcal conjugates for serogroups A+C, C+W+Y or A+C+W+Y can be prepared as described in references 7, 8 and 15. These vaccines have either CRM197, *H. influenzae* protein D or diphtheria toxoid (Dt) as the carrier protein, covalently linked to the saccharides. With conjugates manufactured using essentially the method of reference 8, the following was performed.

For serogroup A, the purified dried polysaccharide was hydrolysed to give an average degree of polymerization (avDP) of 10-11. To remove long polysaccharides, 30 kDa ultrafiltration was used. Q sepharose chromatography was then used to remove short saccharide fragments. Saccharides were subjected to reductive amination, followed by 3 kDa ultrafiltration to remove low MW impurities. The aminated saccharides were concentrated and then activated using the bis N-hydroxysuccinimide ester of adipic acid. This material is suitable for conjugate preparation. The activated ester is mixed with purified CRM197 carrier at a molar saccharide excess of 13:1, with carrier at 45 mg/ml in 0.1M sodium phosphate buffer (pH 7.2). Conjugation is performed at room temperature with magnetic stirring for between 8 and 24 hours. The reaction is stopped by adding $NH_4Cl$ (0.1M final concentration), and the solution is then diluted with 10 mM sodium phosphate pH 7.2. These conditions ensure efficient conjugation and minimise the level of unreacted carrier protein that remains. According to the invention, any remaining unreacted material is diligently removed, with further steps being performed within 2 hours of the dilution mentioned above. Ultrafiltration with a 30 kDa cassette is performed, with 10 mM sodium phosphate (pH 7.2), for up to 4 hours.

For serogroup C, essentially the same process was used, except: nitial hydrolysis was taken to give an avDP between 7 and 16; the conjugation reaction took place for 14-22 hours at room temperature; an additional step was inserted between the conjugation and ultrafiltration steps, with conjugate being purified using hydrophobic interaction chromatography (Phenyl Sepharose fast flow column; 1M ammonium sulphate, 10 mM phosphate buffer pH 7.2; elution by adding buffer with no ammonium sulphate); and the ultrafiltration used a 10 kDa cutoff.

For serogroups W135 and Y, essentially the same processes were used as for serogroup A, except: initial hydrolysis gave an avDP of 20; molar saccharide excess of 12:1.

By these processes, unconjugated carrier levels of less than 1 μg (measured relative to a total CRM197 content of 50 μg) can routinely be achieved for each conjugate.

The four bulk conjugates can be combined in order to give compositions of the invention.

In clinical trial V59P2, conducted in Finland and Germany with 620 subjects aged 12-16 months, five formulations of these mixed conjugates were tested. The doses for each serogroup saccharide, expressed as μg saccharide mass per 0.5 ml dose, were as follows after mixing and dilution:

| Group | MenA | MenC | MenW135 | MenY |
|---|---|---|---|---|
| 1 | 10 | 10 | 10 | 10 |
| 2 | 0 | 10 | 10 | 10 |
| 3 | 10 | 5 | 5 | 5 |
| 4 | 5 | 5 | 5 | 5 |
| 5 | 2.5 | 2.5 | 2.5 | 2.5 |

The vaccines included an aluminium phosphate adjuvant [8]. Unconjugated CRM197 was present at less than 2 μg/ml in the vaccines.

Subjects received an injection at time zero, and 25% of the subjects then received a second dose of the vaccine 4 weeks later.

Sera of patients were collected 1 month after vaccine administration and were tested in a SBA assay against *N. meningitidis* from each serogroup, using human complement. SBA titre increase relative to time zero sera was assessed, with criteria being ≥1:4 and ≥1:8. Anti-capsule titres (GMT) were also measured for each serogroup. Results are shown in Table 1 below.

Thus the trivalent and tetravalent vaccines were both immunogenic in toddlers. The conjugates are immunogenic at saccharide doses as low as 2.5 μg per conjugate. The immune response are boostable, with large SBA titre increases after the second dose. No evidence of carrier suppression was seen in this trial.

It will be understood that the invention is described above by way of example only and modifications may be made while remaining within the scope and spirit of the invention.

TABLE 1

Results of trial V59P2

| Group | A | C | W135 | Y |
|---|---|---|---|---|
| GMT (1 month after 1 dose) | | | | |
| 1 | 3.9 | 6.4 | 7.1 | 8.9 |
| 2 | 2 | 6.1 | 8.3 | 8.5 |
| 3 | 5.7 | 5.2 | 6.9 | 12 |
| 4 | 3.8 | 4.5 | 7.0 | 9.6 |
| 5 | 3.9 | 5.3 | 7.0 | 12 |
| GMT (1 month after 2 doses) | | | | |
| 1 | 27 | 89 | 22 | 37 |
| 2 | 2 | 80 | 20 | 57 |
| 3 | 29 | 76 | 28 | 58 |
| 4 | 14 | 47 | 20 | 35 |
| 5 | 17 | 71 | 23 | 52 |
| % patients with SBA ≥ 1:4 (1 month after 1 dose) | | | | |
| 1 | 33 | 56 | 57 | 58 |
| 2 | 0 | 57 | 60 | 61 |
| 3 | 55 | 49 | 53 | 70 |
| 4 | 37 | 42 | 54 | 64 |
| 5 | 40 | 51 | 57 | 67 |
| % patients with SBA ≥ 1:4 (1 month after 2 doses) | | | | |
| 1 | 100 | 100 | 96 | 96 |
| 2 | 0 | 100 | 73 | 92 |
| 3 | 91 | 96 | 95 | 95 |
| 4 | 84 | 96 | 88 | 96 |
| 5 | 80 | 100 | 80 | 92 |
| % patients with SBA ≥ 1:8 (1 month after 1 dose) | | | | |
| 1 | 25 | 44 | 46 | 48 |
| 2 | 0 | 40 | 50 | 49 |
| 3 | 39 | 34 | 45 | 64 |
| 4 | 23 | 30 | 44 | 51 |
| 5 | 26 | 35 | 40 | 60 |
| % patients with SBA ≥ 1:8 (1 month after 2 doses) | | | | |
| 1 | 92 | 100 | 85 | 93 |
| 2 | 0 | 100 | 64 | 92 |
| 3 | 87 | 96 | 95 | 82 |
| 4 | 60 | 92 | 77 | 92 |
| 5 | 72 | 92 | 72 | 88 |

REFERENCES

The Contents of which are Hereby Incorporated by Reference

[1] Baklaic et al. (1983) *Infect. Immun.* 42:599-604.
[2] Armand et al. (1982) *J. Biol. Stand.* 10:335-339.
[3] Cadoz et al. (1985) *Vaccine* 3:340-342.
[4] Jones (2001) *Curr Opin Investig Drugs* 2:47-49.
[5] Costantino et al. (1992) *Vaccine* 10:691-8.
[6] Lieberman et al. (1996) *JAMA* 275:1499-503.
[7] WO02/058737.
[8] WO03/007985.
[9] Rennels et al. (2002) *Pediatr Infect Dis J* 21:978-979.
[10] Campbell et al. (2002) *J Infect Dis* 186:1848-1851.
[11] Herzenberg et al. (1980) *Nature* 285: 664-667.
[12] Dagan et al. (1998) *Infect Immun* 66:2093-2098.
[13] Burrage et al. (2002) *Infect Immun* 70:4946-4954.
[14] Reddin et al. (2001) *FEMS Immunol Med Microbiol* 31:153-162.
[15] WO02/00249.
[16] EP-B-0831901.
[17] Ramsay et al. (2001) *Lancet* 357(9251):195-196.
[18] Lindberg (1999) *Vaccine* 17 Suppl 2:S28-36.
[19] Buttery & Moxon (2000) *J R Coll Physicians Lond* 34:163-168.
[20] Ahmad & Chapnick (1999) *Infect Dis Clin North Am* 13:113-33, vii.
[21] Goldblatt (1998) *J. Med. Microbiol.* 47:563-567.
[22] European patent 0477508.
[23] U.S. Pat. No. 5,306,492.
[24] WO98/42721.
[25] Dick et al. in *Conjugate Vaccines* (eds. Cruse et al.) Karger, Basel, 1989, 10:48-114.
[26] Chapter 10 of *Vaccine Protocols* (2nd edition, 2003). ISBN: 1-59259-399-2.
[27] Hermanson *Bioconjugate Techniques*, Academic Press, San Diego (1996) ISBN: 0123423368.
[28] WO99/42130
[29] U.S. Pat. No. 4,711,779.
[30] WO03/080678.
[31] Glode et al. (1979) *J Infect Dis* 139:52-56
[32] WO94/05325; U.S. Pat. No. 5,425,946.
[33] United Kingdom patent application 0323103.2.
[34] Vaccines. (eds. Plotkin & Orenstein). 4th edition, 2004, ISBN: 0-7216-9688-0.
[35] U.S. Pat. No. 4,709,017.
[36] WO93/25210.
[37] U.S. Pat. No. 5,917,017.
[38] WO00/48638.
[39] Del Guidice et al. (1998) *Molecular Aspects of Medicine* 19:1-70.
[40] Anonymous (January 2002) Research Disclosure, 453077.
[41] Anderson (1983) *Infect Immun* 39(1):233-238.
[42] Anderson et al. (1985) *J Clin Invest* 76(1):52-59.
[43] EP-A-0372501.
[44] EP-A-0378881.
[45] EP-A-0427347.
[46] WO93/17712
[47] WO94/03208.
[48] WO98/58668.
[49] EP-A-0471177.
[50] WO91/01146
[51] Falugi et al. (2001) *Eur J Immunol* 31:3816-3824.
[52] EP-A-0594610.
[53] Ruan et al. (1990) *J Immunol* 145:3379-3384.
[54] WO00/56360.
[55] Kuo et al. (1995) *Infect Immun* 63:2706-13.
[56] WO02/091998.
[57] WO01/72337
[58] WO00/61761.
[59] Lees et al. (1996) *Vaccine* 14:190-198.
[60] WO95/08348.
[61] U.S. Pat. No. 4,882,317.
[62] U.S. Pat. No. 4,695,624
[63] Porro et al. (1985) *Mol Immunol* 22:907-919.
[64] EP-A-0208375
[65] WO00/10599
[66] Gever et al. Med. Microbiol. Immunol, 165:171-288 (1979).
[67] U.S. Pat. No. 4,057,685.
[68] U.S. Pat. Nos. 4,673,574; 4,761,283; 4,808,700.

[69] U.S. Pat. No. 4,459,286.
[70] U.S. Pat. No. 4,965,338
[71] U.S. Pat. No. 4,663,160.
[72] U.S. Pat. No. 4,761,283
[73] U.S. Pat. No. 4,356,170
[74] Lamb et al. (2000) *Dev Biol* (Basel) 103:251-258.
[75] Lamb et al. (2000) *Journal of Chromatography A* 894:311-318.
[76] Gennaro (2000) *Remington: The Science and Practice of Pharmacy.* 20th ed. ISBN: 0683306472.
[77] Almeida & Alpar (1996) *J. Drug Targeting* 3:455-467.
[78] Agarwal & Mishra (1999) *Indian J Exp Biol* 37:6-16.
[79] *Vaccine Design* . . . (1995) eds. Powell & Newman. ISBN: 030644867X. Plenum.
[80] WO00/23105.
[81] WO90/14837.
[82] U.S. Pat. No. 5,057,540.
[83] WO96/33739.
[84] EP-A-0109942.
[85] WO96/11711.
[86] WO00/07621.
[87] Barr et al. (1998) *Advanced Drug Delivery Reviews* 32:247-271.
[88] Sjolanderet et al. (1998) *Advanced Drug Delivery Reviews* 32:321-338.
[89] Niikura et al. (2002) *Virology* 293:273-280.
[90] Lenz et al (2001) *J Immunol* 166:5346-5355.
[91] Pinto et al. (2003) *J Infect Dis* 188:327-338.
[92] Gerber et al. (2001) *Virol* 75:4752-4760.
[93] WO03/024480
[94] WO03/024481
[95] Gluck et al. (2002) *Vaccine* 20:B10-B16.
[96] EP-A-0689454.
[97] Johnson et al. (1999) *Bioorg Med Chem Lett* 9:2273-2278.
[98] Evans et al. (2003) *Expert Rev Vaccines* 2:219-229.
[99] Meraldi et al (2003) *Vaccine* 21:2485-2491.
[100] Pajak et al. (2003) *Vaccine* 21:836-842.
[101] Kandimalla et al. (2003) *Nucleic Acids Research* 31:2393-2400.
[102] WO02/26757.
[103] WO99/62923.
[104] Krieg (2003) *Nature Medicine* 9:831-835.
[105] McCluskie et al. (2002) *FEMS Immunology and Medical Microbiology* 32:179-185.
[106] WO98/40100.
[107] U.S. Pat. No. 6,207,646.
[108] U.S. Pat. No. 6,239,116.
[109] U.S. Pat. No. 6,429,199.
[110] Kandimalla et al. (2003) *Biochemical Society Transactions* 31 (part 3):654-658.
[111] Blackwell et al. (2003) *J Immunol* 170:4061-4068.
[112] Krieg (2002) *Trends Immunol* 23:64-65.
[113] WO01/95935.
[114] Kandimalla et al. (2003) *BBRC* 306:948-953.
[115] Bhagat et al. (2003) *BBRC* 300:853-861.
[116] WO03/035836.
[117] WO95/17211.
[118] WO98/42375.
[119] Beignon et al. (2002) *Infect Immun* 70:3012-3019.
[120] Pizza et al. (2001) *Vaccine* 19:2534-2541.
[121] Pizza et al. (2000) *Int J Med Microbiol* 290:455-461.
[122] Scharton-Kersten et al. (2000) *Infect Immun* 68:5306-5313.
[123] Ryan et al. (1999) *Infect Immun* 67:6270-6280.
[124] Partidos et al. (1999) *Immunol Lett* 67:209-216.
[125] Peppoloni et al. (2003) *Expert Rev Vaccines* 2:285-293.
[126] Pine et al. (2002) *J Control Release* 85:263-270.
[127] Domenighini et al. (1995) *Mol Microbiol* 15:1165-1167.
[128] WO99/40936.
[129] WO99/44636.
[130] Singh et al] (2001) *J Cont Release* 70:267-276.
[131] WO99/27960.
[132] U.S. Pat. No. 6,090,406.
[133] U.S. Pat. No. 5,916,588
[134] EP-A-0626169.
[135] WO99/52549.
[136] WO01/21207.
[137] WO01/21152.
[138] Andrianov et al. (1998) *Biomaterials* 19:109-115.
[139] Payne et al. (1998) *Adv Drug Delivery Review* 31:185-196.
[140] Stanley (2002) *Clin Exp Dermatol* 27:571-577.
[141] Jones (2003) *Curr Opin Investig Drugs* 4:214-218.
[142] WO99/11241.
[143] WO94/00153.
[144] WO98/57659.
[145] European patent applications 0835318, 0735898 and 0761231.
[146] WO03/009869.
[147] Balmer & Borrow (2004) *Expert Rev Vaccines* 3:77-87.
[148] Kanra et al. (1999) *The Turkish Journal of Paediatrics* 42:421-427.
[149] Ravenscroft et al. (2000) *Dev Biol (Basel)* 103: 35-47.
[150] WO97/00697.
[151] WO96/37222; U.S. Pat. No. 6,333,036.
[152] Watson (2000) *Pediatr Infect Dis J* 19:331-332.
[153] Rubin (2000) *Pediatr Clin North Am* 47:269-285, v.
[154] Jedrzejas (2001) *Microbiol Mol Biol Rev* 65:187-207.
[155] Zielen et al. (2000) *Infect. Immun.* 68:1435-1440.
[156] Darkes & Plosker (2002) *Paediatr Drugs* 4:609-630.
[157] WO2004/032958
[158] Podda et al. (1991) *Vaccine* 9:741-745.
[159] Gerlich et al. (1990) *Vaccine* 8 Suppl:S63-68 & 79-80.
[160] WO93/24148.
[161] Sutter et al. (2000) *Pediatr Clin North Am* 47:287-308.
[162] Zimmerman & Spann (1999) *Am Fam Physician* 59:113-118, 125-126.
[163] Bell (2000) *Pediatr Infect Dis J* 19:1187-1188.
[164] Iwarson (1995) *APMIS* 103:321-326.
[165] Lyng & Betzon (1987) *J Biol Stand* 15:27-37.

The invention claimed is:

1. A composition for immunising a patient against a disease caused by Neisseria meningitidis, comprising at least two of: (a) a conjugate of (i) the capsular saccharide of serogroup A *N. meningitidis* and (ii) a carrier protein; (b) a conjugate of (i) the capsular saccharide of serogroup C *N. meningitidis* and (ii) a carrier protein; (c) a conjugate of (i) the capsular saccharide of serogroup W135 *N. meningitidis* and (ii) a carrier protein; (d) a conjugate of (i) the capsular saccharide of serogroup Y *N. meningitidis* and (ii) a carrier protein, characterised in that (1) at least two of said conjugates (a), (b), (c) and (d) use the same carrier protein, wherein said same carrier protein is a common carrier protein, and (2) the composition includes the common carrier protein in an unconjugated form, wherein the concentration of the unconjugated common carrier protein is >0.01 µg/ml but <2 µg/ml.

2. The composition of claim 1, comprising the conjugate of (a) and the conjugate of (b).

3. The composition of claim 1, comprising the conjugate of (a), the conjugate of (b), the conjugate of (c), and the conjugate of (d).

4. The composition of claim 1, wherein each of the conjugates is conjugated to the common carrier protein selected from diphtheria toxoid; tetanus toxoid; CRM197; and protein D from *H. influenzae*.

5. The composition of claim 4, wherein the common carrier protein is diphtheria toxoid.

6. The composition of claim 4, wherein the common carrier protein is *H. influenzae* protein D.

7. The composition of claim 1, wherein the total concentration of the common carrier protein in the composition is less than 100 µg/ml.

8. The composition of claim 1, formulated for intramuscular injection.

9. The composition of claim 1, wherein the composition does not include any mercurial material.

10. The composition of claim 1, in aqueous form.

11. The composition of claim 2, comprising the conjugate of (a), the conjugate of (b), the conjugate of (c), and the conjugate of (d).

12. The composition of claim 2, wherein each of the conjugates is conjugated to the common carrier protein selected from diphtheria toxoid; tetanus toxoid; CRM197; and protein D from *H. influenzae*.

13. The composition of claim 3, wherein each of the conjugates is conjugated to the common carrier protein selected from diphtheria toxoid; tetanus toxoid; CRM197; and protein D from *H. influenzae*.

14. The composition of claim 12, wherein the common carrier protein is diphtheria toxoid.

15. The composition of claim 13, wherein the common carrier protein is diphtheria toxoid.

16. The composition of claim 12, wherein the common carrier protein is *H. influenzae* protein D.

17. The composition of claim 13, wherein the common carrier protein is *H. influenzae* protein D.

18. The composition of claim 2, wherein the total concentration of the common carrier protein in the composition is less than 100 µg/ml.

19. The composition of claim 3, wherein the total concentration of the common carrier protein in the composition is less than 100 µg/ml.

20. The composition of claim 4, wherein the total concentration of the common carrier protein in the composition is less than 100 µg/ml.

21. The composition of claim 12, wherein the total concentration of the common carrier protein in the composition is less than 100 µg/ml.

22. The composition of claim 13, wherein the total concentration of the common carrier protein in the composition is less than 100 µg/ml.

23. The composition of claim 2, formulated for intramuscular injection.

24. The composition of claim 3, formulated for intramuscular injection.

25. The composition of claim 4, formulated for intramuscular injection.

26. The composition of claim 12, formulated for intramuscular injection.

27. The composition of claim 13, formulated for intramuscular injection.

28. The composition of claim 2, wherein the composition does not include any mercurial material.

29. The composition of claim 3, wherein the composition does not include any mercurial material.

30. The composition of claim 4, wherein the composition does not include any mercurial material.

31. The composition of claim 12, wherein the composition does not include any mercurial material.

32. The composition of claim 13, wherein the composition does not include any mercurial material.

33. The composition of claim 2, in aqueous form.

34. The composition of claim 3, in aqueous form.

35. The composition of claim 4, in aqueous form.

36. The composition of claim 12, in aqueous form.

37. The composition of claim 13, in aqueous form.

* * * * *